United States Patent
Brown et al.

(10) Patent No.: US 6,866,613 B1
(45) Date of Patent: Mar. 15, 2005

(54) PROGRAM FOR MONITORING CUMULATIVE FITNESS ACTIVITY

(75) Inventors: Michael Wayne Brown, Georgetown, TX (US); Kelvin Roderick Lawrence, Round Rock, TX (US); Michael A. Paolini, Round Rock, TX (US)

(73) Assignee: International Business Machines Corporation, Armonk, NY (US)

( * ) Notice: Subject to any disclaimer, the term of this patent is extended or adjusted under 35 U.S.C. 154(b) by 28 days.

(21) Appl. No.: 10/686,320

(22) Filed: Oct. 14, 2003

Related U.S. Application Data (62) Division of application No. 09/561,115, filed on Apr. 28, 2000, now Pat. No. 6,746,371.

(51) Int. Cl.$^7$ .............................................. A63B 21/00
(52) U.S. Cl. ............................... 482/8; 482/9; 482/900
(58) Field of Search ......................... 482/1–9, 900–902

(56) References Cited

U.S. PATENT DOCUMENTS

| | | |
|---|---|---|
| 4,817,940 A | 4/1989 | Shaw et al. |
| 4,828,257 A | 5/1989 | Dyer et al. |
| 4,891,785 A | 1/1990 | Donohoo |
| 5,204,670 A | 4/1993 | Stinton |
| 5,213,555 A | 5/1993 | Hood et al. |
| 5,335,188 A | 8/1994 | Brisson |
| 5,387,164 A | 2/1995 | Brown, Jr. |
| 5,435,799 A | 7/1995 | Lundin |
| 5,598,849 A | 2/1997 | Browne |
| 5,702,323 A | 12/1997 | Poulton |
| 5,785,632 A | 7/1998 | Greenberg et al. |
| 5,799,281 A | 8/1998 | Login et al. |
| 5,816,443 A | 10/1998 | Bustos |
| 5,888,172 A | 3/1999 | Andrus et al. |
| 5,937,387 A | 8/1999 | Summerell et al. |
| 5,947,868 A | 9/1999 | Dugan |
| 5,957,699 A | 9/1999 | Peterson et al. |
| 5,973,696 A | 10/1999 | Agranat et al. |
| 5,976,083 A | 11/1999 | Richardson et al. |
| 5,984,839 A | 11/1999 | Corkum |
| 6,042,519 A | 3/2000 | Shea |
| 6,193,631 B1 * | 2/2001 | Hickman ........................ 482/8 |
| 6,450,922 B1 * | 9/2002 | Henderson et al. ............. 482/8 |
| 6,464,618 B1 | 10/2002 | Shea |
| 6,503,173 B2 * | 1/2003 | Clem ............................ 482/8 |
| 6,601,016 B1 | 7/2003 | Brown et al. |
| 6,604,023 B1 | 8/2003 | Brown et al. |

* cited by examiner

*Primary Examiner*—Glenn E. Richman
(74) *Attorney, Agent, or Firm*—Marilyn S. Dawkins; Dillon & Yudell LLP (57) ABSTRACT

In accordance with the method, system and program of the present invention, at least one type of exercise indicator signal associated with exercise performed by a particular user is received from a particular exercise machine in a common transmittable data format at a portable computer system provided the particular user. Cumulative fitness activity is computed and stored for the particular user at the portable computer system utilizing the at least one type of exercise indicator signal and previously accumulated fitness activity data at the portable computer system, such that an independent portable computer system associated with the particular user monitors the real-time cumulative fitness activity of the particular user from at least one type of exercise indicator signal received from at least one exercise machine over a period of time.

10 Claims, 8 Drawing Sheets

PROGRAM FOR MONITORING CUMULATIVE FITNESS ACTIVITY

RELATED U.S. APPLICATION DATA

This application is a divisional of prior application Ser. No. 09/561,115, filed on Apr. 28, 2000, and entitled "Managing Fitness Activity Across Diverse Exercise Machines Utilizing a Portable Computer System," now U.S. Pat. No. 6,746,371, which is incorporated herein by reference.

This application is related to:

U.S. patent application Ser. No. 09/561,130 filed Apr. 28, 2000, now abandoned;

U.S. patent application Ser. No. 09/561,426 filed Apr. 28, 2000, now U.S. Pat. No. 6,601,016, U.S. patent application Ser. No. 09/561,134 filed Apr. 28, 2000, now abandoned; and U.S. patent application Ser. No. 09/561,422 filed Apr. 28, 2000;

all of which are incorporated herein by reference.

BACKGROUND OF THE INVENTION

1. Technical Field

The present invention relates to an improved method, system and program for monitoring fitness activity in general and, in particular, to an improved method, system and program for managing fitness activity across diverse exercise machines with a portable computer system. Still more particularly, the present invention relates to a method, system and program for monitoring the real-time cumulative fitness activity of a user from fitness activity data received from a plurality of diverse exercise machines over a period of time at a single, portable computer system.

2. Description of the Prior Art

A fitness craze has recently swept the United States and other countries. From fat-free potato chips to treadmills, people around the world have become obsessed with weight loss and healthy living. Accordingly, record numbers of new fitness products/exercise equipment from multiple manufacturers have emerged to meet this obsession (including stair climbers, treadmills, recumbent bicycles, ski machines, rowing machines, weight lifting machines, and the like).

Many pieces of exercise equipment, when utilized regularly, are very useful for weight loss, for improving cardiovascular stamina, and for strengthening various muscles. Most exercise equipment includes a monitoring device that may include a pulse monitor, a distance meter, a rate monitor, a time monitor, a strain gauge, an accelerometer and/or any other sensor for measuring the physical activity/performance level of an user on the equipment. Moreover, monitoring devices typically request personal data from the user such as age, weight and desired physical fitness level. The monitoring device utilizes the personal data in combination with physical exertion and heart rate to estimate calories burned, fitness levels met, and other fitness related data. In addition, the monitor may adjust the resistance or speed of a piece of exercise equipment in order to aid the user in reaching and/or maintaining a fitness level for that exercise session.

One limiting factor of many exercise machines and monitors is that the user must reenter their personal data to the monitor each time the user utilizes an exercise machine. In addition, most exercise machines do not have a previous history of the user from which to provide data about improvement and to provide additional fitness goals.

However, one solution to providing a history for a user is provided in U.S. Pat. No. 5,335,188 ('188). In '188, a speed and time elapsed of an exercise session on a bicycle is recorded. The user may choose to save the speed and time of an exercise session under an identifier for the user. The user may later select a particular exercise session as a standard of performance for subsequent performances whereby each subsequent performance is compared with the selected exercise session. However, while the bicycle monitor memory stores exercise sessions for a particular user at that bicycle, in a club or other venue where multiple bicycles are provided, the user may not always have access to the bicycle at which the session data is stored in order to add to the data.

Another limiting factor of many exercise machines is that they operate and monitor the user independent of one another. However, cross-training across multiple machines is popular in order to exercise different parts of the body. An individual may spend 20 minutes on a treadmill working a hills program where the monitor for the treadmill calculates a certain number of calories burned and other fitness related data. The individual may then move to a rowing machine that does not realize that the user has already worked for 20 minutes and thus calculates calories burned and other fitness related data as if the user only worked out on the rowing machine. An overall fitness level achieved by the user after working on both machines is not provided.

One solution to cross-training across multiple machines is provided in U.S. Pat. No. 5,598,849 ('849). In '849, an individual is provided with a user monitor that has a preferred exercise regimen of physical parameters such as heart rate stored therein. The user is required to monitor at least one physical parameter with the assistance of the user monitor and is preferably required during exercise to control his exercise to maintain the physical parameter as closely as possible to the preset values. After exercising is completed, the monitored physical parameters are proffered from the user monitor and sent to a master data processing system where the monitored parameters are stored and compared with the preset parameters in order to develop a fitness profile. However, a real-time fitness profile is not provided by the prior art. In addition, the exercise regimen is not alterable during the workout. Moreover, the user monitor is limited in that it operates independent of the exercise machine and therefore does not provide feedback to the exercise machine in order that resistance or another variable may be adjusted.

Moreover, another limiting factor of many exercise machines is that they are boring to utilize because of their inability to encourage a user to continue exercising. Display screens that depict a user's location within a selected exercise program may be provided; however, they typically include dull graphics. One solution to improving graphical rendering is provided in U.S. Pat. No. 5,947,868 ('868). In the '868 patent, an exercise monitor outputs a signal representative of the performance level of a user utilizing the exercise equipment (e.g. pulse rate, distance traveled, time exercised, rate of exercise, etc.). The performance level signal then is fed to a video game player wirelessly or via a cable.

The video game player preferably utilizes a hand-held video game player. To simulate the user, the output from the exercise monitor is utilized to control the video game character's performance level within a video game that runs on the video game player. For example, the lifetime of a video game character may be increased by peddling faster.
}

However, while the video game player provides a graphical venue by which the user controls a video game character according to their fitness level, other types of graphical rendering, other than a video game are not provided. In addition, in order to utilize the video game player, a monitor that supplies a particular type of performance level signal must be coupled to the exercise machine. Another limiting factor of many exercise machines is that they do not provide a display that is adjustable dependent upon the user. For example, existing systems are limited in that they do not offer displaying output from an exercise machine in a particular language, dependent upon the user.

Therefore, in view of the aforementioned, it would be advantageous to provide a personal electronic exercise monitor that operates in real-time to transmit control signal to multiple diverse exercise machines to control the movement of the exercise machines, proffer fitness data from multiple diverse exercise machines, utilize the fitness data from each exercise machine to update cumulative fitness activity over a period of time, adjust the control signal to meet fitness goals and control a graphical rendering of current exertion and totals that are selected by the individual. In addition, it would be desirable to provide a personal electronic exercise monitor that transmits personal data and/or exercise program selections to an exercise machine monitor such that it is not necessary for a user to re-enter the data at multiple diverse exercise machines.

SUMMARY OF THE INVENTION

In view of the foregoing, it is therefore an object of the present invention to provide an improved method, system and program for monitoring exercise.

It is another object of the present invention to provide an improved method, system and program for managing fitness activity across diverse exercise machines with a portable computer system.

It is yet another object of the present invention to provide an improved method, system and program for monitoring the real-time cumulative fitness activity of a user from fitness activity data received from a plurality of diverse exercise machines over a period of time at a single data processing system.

In accordance with the method, system and program of the present invention, at least one type of exercise indicator signal associated with exercise performed by a particular user is received from a particular exercise machine in a common transmittable data format at a portable computer system for a particular user. Cumulative fitness activity is computed and stored for the particular user at the portable computer system utilizing the at least one type of exercise indicator signal and previously accumulated fitness activity data at the portable computer system, such that an independent portable computer system associated with the particular user monitors the real-time cumulative fitness activity of the particular user from at least one type of exercise indicator signal received from at least one exercise machine over a period of time.

All objects, features, and advantages of the present invention will become apparent in the following detailed written description.

DESCRIPTION OF THE DRAWINGS

The invention itself as will as a preferred mode of use, further objects, and advantages thereof, will best be understood by reference to the following detailed description of an illustrative embodiment when read in conjunction with the accompanying drawings, wherein.

DESCRIPTION OF A PREFERRED EMBODIMENT

The present invention may be executed in a variety of systems, including a variety of computing systems and electronic devices under a number of different operating systems. In a preferred embodiment of the present invention, the computer system is a portable computing system such as a notebook computer, a palmtop computer, a personal digital assistant, a telephone or other electronic computing system that may also incorporate communications features that provides for telephony, enhanced telephony, messaging and information services. However, the computer system may also be, for example, a desktop computer, a network computer, a midrange computer or a mainframe computer. Preferably, in order to enable at least one of these communications features, the computer system is able to be connected to a network, such as the Internet by either a wired link or wireless link. In addition, the computer system may be a standalone system or part of a network such as a local-area network (LAN) or a wide-area network (WAN). Therefore, in general, the present invention is preferably executed in a computer system that performs computing tasks such as manipulating data in storage that is accessible to the computer system. In addition, the computer system includes at least one output device and at least one input device.

Figure 1:
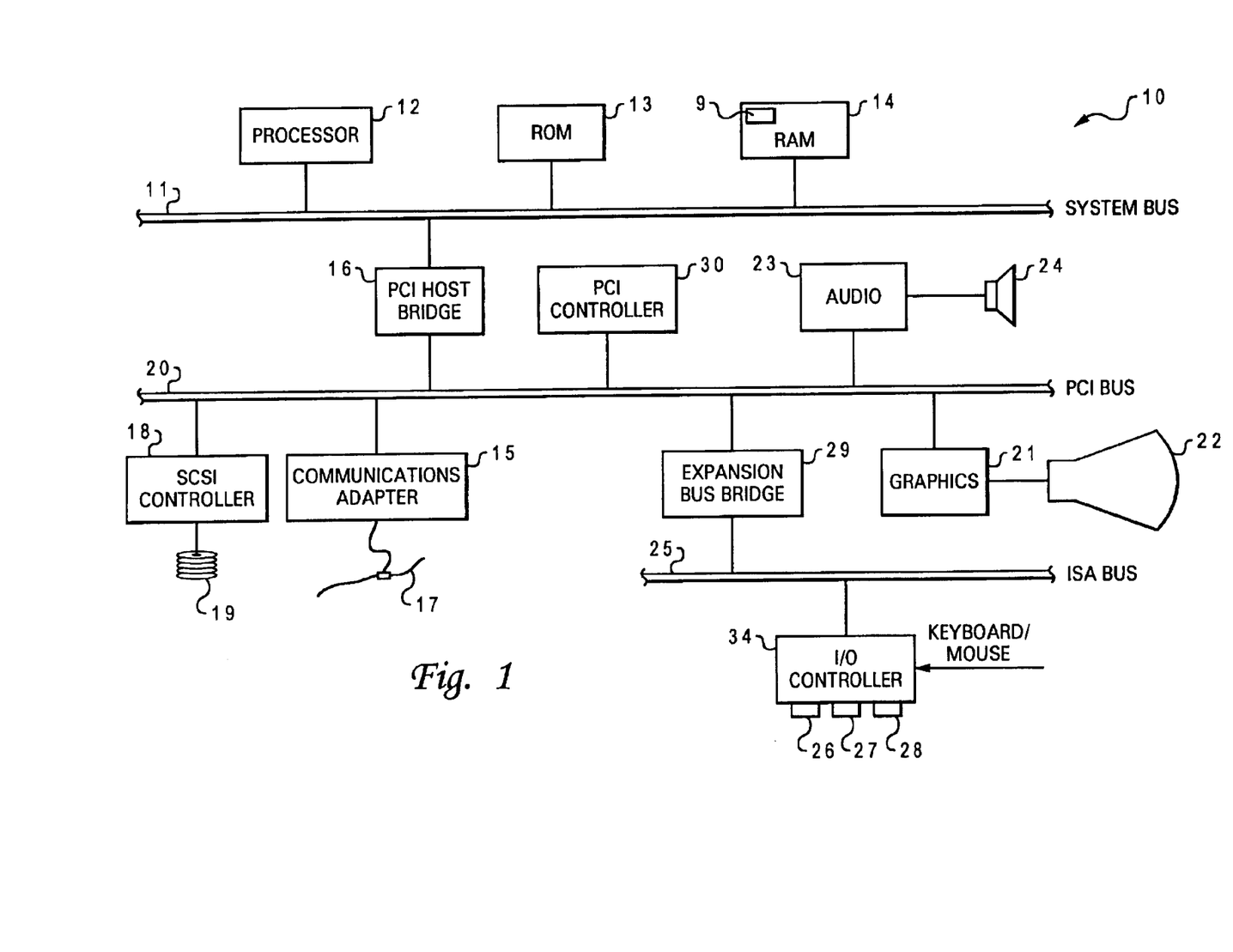
FIG. 1 depicts one embodiment of a data processing system with which the method, system and program of the present invention may advantageously be utilized.

Referring now to the drawings and in particular to FIG. 1, there is depicted a block diagram of one embodiment of a computer system that may utilize the present invention. As depicted, data processing system 10 includes at least one processor 12, which is coupled to system bus 11. Each processor 12 is a general-purpose processor, such as IBM's PowerPC™ processor that, during normal operation, processes data under the control of operating system and application software stored in random access memory (RAM) 14 and Read Only Memory (ROM) 13. The operating system preferably provides a graphical user interface (GUI) to the user. Application software contains instructions that when executed on processor 12 carry out the operations depicted in the flowcharts of FIGS. 6, 7, 8, 9 and others described herein.

Processors 12 are coupled via system bus 11 and Peripheral Component Interconnect (PCI) host bridge 16 to PCI local bus 20. PCI host bridge 16 provides a low latency path through which processor 12 may directly access PCI devices mapped anywhere within bus memory and/or I/O address spaces. PCI host bridge 16 also provides a high bandwidth path for allowing PCI devices to directly access RAM 14.

PCI local bus 20 interconnects a number of devices for communication under the control of PCI controller 30. These devices include a Small Computer System Interface (SCSI) controller 18, which provides an interface to SCSI hard disk 19, and communications adapter(s) 15, which interface data processing system 10 to at least one data communication network 17 comprising wired and/or wireless network communications. In addition, an audio adapter 23 is attached to PCI local bus 20 for controlling audio output through speaker 24. A graphics adapter 21 is also attached to PCI local bus 20 for controlling visual output through display monitor 22. In alternate embodiments of the present invention, additional peripheral components may be added. For example, in alternate embodiments, a tactile display component may be provided.

PCI local bus 20 is further coupled to an Industry Standard Architecture (ISA) bus 25 by an expansion bus bridge 29. As shown, ISA bus 25 has an attached I/O (Input/Output) controller 34 that interfaces data processing system 10 to peripheral input devices such as a keyboard and mouse (not illustrated) and supports external communication via parallel, serial and universal serial bus (USB) ports 26, 27, and 28, respectively.

Figure 2:
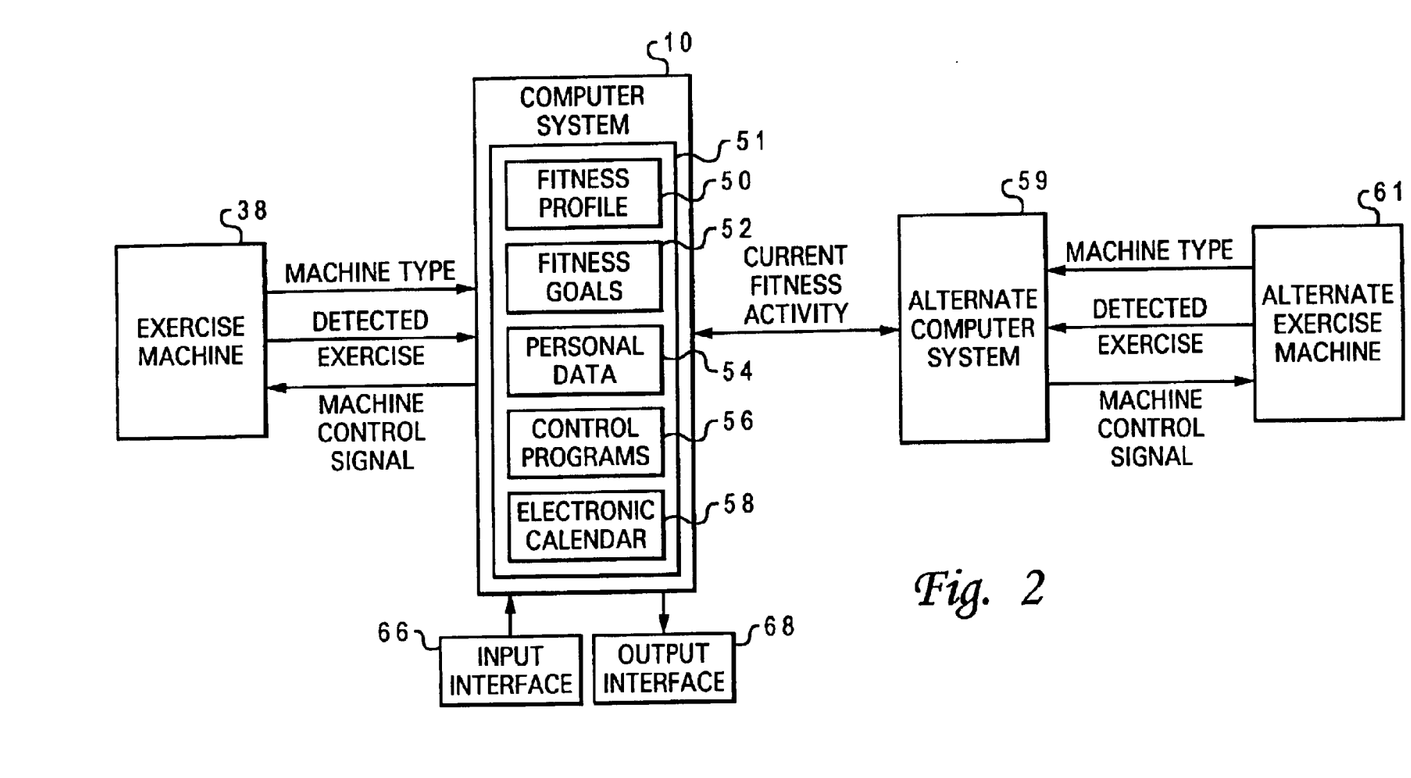
FIG. 2 illustrates a preferred embodiment of a system for utilizing a personal electronic exercise monitor in accordance with the method, system and program of the present invention.

With reference now to FIG. 2, there is depicted one embodiment of a block diagram of a system for utilizing a personal electronic exercise monitor in accordance with the method, system and program of the present invention. As depicted, computer system 10 preferably acts as a personal electronic exercise monitor that accesses, interprets, and controls fitness data across diverse exercise machine platforms. A fitness profile 50, fitness goals 52, personal data 54, control programs 56, and electronic calendar 58 are preferably stored within a data storage medium 51 of computer system 10. While in the present embodiment data storage medium is depicted at internally accessible to computer system 10, in alternate embodiments, data storage medium 51 may be externally or remotely accessible to computer system 10. In addition, the data stored in data storage medium 51 is preferably updatable through downloads from other sources to computer system 10. Moreover, the data stored on computer system 10 is preferably efficiently stored in a particular data transmission format, such the extensible mark-up language (XML), or is easily convertible into the data transmission format.

Computer system 10 preferably communicates with multiple diverse exercise machines, such as exercise machine 38, via a bi-directional communications medium (or across a communication interface). In addition, as will be further described, computer system 10 may communicate with alternate server systems via a bi-directional communication medium. The communications medium may include wired or wireless communications or other communications media that enables bi-directional transmission of data. Moreover, the communications medium may include a link to a network, such as the Internet, or a direct data link.

In a wired embodiment of the communications medium, for example, exercise machine 38 is connected to computer system 10 via parallel, serial, or USB ports, or the communication adapter as depicted in FIG. 1. In a wireless embodiment of the communications medium, for example, exercise machine 38 is wirelessly connected to computer system 10 via infrared, radio frequency (RF), cellular and other wireless transmissions which are detected by computer system 10.

Data exchange across the communications medium is advantageously performed in at least one of multiple available data transmission protocols and is preferably supported by a common data structure format, such as the extensible mark-up language (XML) data structure format. Data transmission protocols may include, but are not limited to, Transmission Control Protocol (TCP), Internet Protocol (IP), Hypertext Transfer Protocol (HTTP), and Bluetooth. In addition, data may be transmitted in a secure manner via encryption or by technologies such as secure socket layer (SSL) or virtual private networks (VPN).

An example of an XML data file that might be transmitted from computer system 10 to exercise machine 38, as depicted below, preferably contains data that is distinguished by attributes on elements and may be wrapped within a larger element. For example, the data attributed to element "<TimeStamp> </TimeStamp>" designates the time that the data was attributed to the XML data file.

<TREADMILL TimeStamp="888965153" MachineType="Arc2000" UserID="JANEXYZ" Speed="30" Elevation="5">.

In addition, in an alternate example, the XML data file might be formatted utilizing elements, as illustrated below.

<TimeStamp>888965153</TimeStamp>
<MachineType>Arc2000</MachineType>
<UserID>JANEXYZ</UserID>
<Speed>30</Speed>
<Elevation>5</Elevation>.

In the example, as will be further described, exercise machine 38 would receive the example XML data file and utilize the XML data file to control operation of exercise machine 38. The above described XML data file example is intended as a functional example of an XML data file that would control the speed and elevation of a treadmill. The elements, format of the elements and data included with the elements is provided to depict an example and is not intended to limit the types of elements, format of elements or data included with elements that are in an XML data file.

In the example of the XML data format as the common transmittable data format, a data validation file such as a document type definition (DTD) or schema is preferably utilized to validate XML data files. In addition, a schema preferably translates multiple XML data files. Moreover, a style sheet such as an extensible stylesheet language (XSL) file is preferably utilized to provide a style specification for the XML data at the receiving system. In particular, DTDs, schemas, and XSL files may be, for example, transmitted with an XML data file to a receiving system or downloaded at the receiving system from an alternate source. In the present example, the DTD or schema would verify that all the data required for transmittal to a particular exercise machine is included in the XML data file. For example, a speed and elevation may be required to validate the XML data file.

Exercise machine 38 advantageously transmits measurements in the common transmittable data structure format from real-time monitoring systems associated with exercise machine 38 including, but not limited to a pulse monitor, a distance meter, a rate monitor, a time monitor, a strain gauge, an accelerometer and/or any other sensor for measuring the physical activity/performance level of a user on a piece of equipment.

Detected exercise signals, such as a pulse, distance, rate, time, strain, etc, are preferably transmitted from exercise machine 38 in a common transmittable data format. For example, an example of an XML data file for a pulse monitor is described below where a user's pulse is measured between a particular time period at 80 beats per minute. In addition, an alternate form of XML formatting may be utilized.

<TimeRange>888965153,888965160</TimeRange>
    <MachineID>45365</MachineID>
    <MachineType>PulseMonitor</MachineType>
    <Rate>80</Rate>.

Computer system 10 is preferably enabled to compute current fitness activity based on the detected exercise in the form of a pulse, distance, rate, time, strain, acceleration, and any other sensed value that may be utilized to compute current fitness activity. In addition, in calculating current fitness activity, factors such as previously accumulated fitness activity stored in fitness profile 50, personal data 54, and the type of exercise machine are utilized to compute a realistic fitness assessment. Thereby, computer system 10 is enabled to compute and store cumulative real-time fitness activity within fitness profile 50 over a selected time period or session from across multiple diverse exercise machines.

Cumulative fitness activity over a selected time period is preferably computed from summing previously accumulated fitness activity for the selected time period with the current fitness activity. In summing the previously accumulated fitness activity and current fitness activity, computer system 10 may adjust the cumulative total to more closely reflect the fitness gained as a result of exercising on multiple machines over a period of time. For example, if a user exercises for an hour across three different exercise machines, the amount of calories burned by the user actually increases with prolonged exercise over a particular amount of time determined for that user and therefore is adjusted in the cumulative fitness activity.

In addition, to storing cumulative real-time fitness activity for a user over a particular period of time, individual sessions of fitness activity may also be recorded. For example, if a user exercises on a treadmill for 20 minutes and a rowing machine for 20 minutes, a cumulative fitness profile may be calculated and stored in fitness profile 50. In addition, fitness activity achieved from exercise on the treadmill and rowing machine may be stored as separate exercise sessions. Moreover, in addition to calculating cumulative fitness activity according to previously accumulated fitness activity, personal data 54 and the type of exercise machine, the types of food eaten by the user that day, fluid intake, medication usage and environmental exposure may be utilized to determine cumulative fitness activity data.

In particular, in addition to receiving detected exercise signals from exercise machine 38, detected exercise may be input by a user via input interface 66 or from another monitoring device. For example, a user may count the number of jumping jacks that they perform during a break between utilizing exercise machines. The number of jumping jacks can be entered into computer system 10 via an input interface 66 and computer system 10 computes fitness activity data for the jumping jacks and updates the cumulative real-time fitness activity data.

Input interface 66 may include, but is not limited to including, a keyboard, a mouse, a stylus, a vocal recognition system, a tactile-detectable device, a biometric detection device, a disk drive, a personal storage device adapter, and other devices which allow user input to computer system 10. Preferably, input interface 66 provides an interface with computer system 10 through which a user may supplement data provided by exercise machine 38. In addition, input interface 66 preferably provides an interface with computer system 10 through which a user may customize the functions performed by computer system 10 and data stored therein.

In addition, in an alternate embodiment, other monitoring systems may be associated with computer system 10. For example, a pulse monitor may be associated with computer system 10 that detects the pulse of a user as the user exercises on exercise machine 38, independent of exercise machine 38. In another example, a pulse rate monitor may record a pulse rate for a user over a period of time, such as during a foot race, and transmit the recorded exercise signals to computer system 10, independent of an exercise machine. Therefore, an exercise machine need not include monitoring systems for detecting health parameters during exercise. In addition, the cumulative fitness activity data calculated at computer system 10 may be supplemented with exercise measurements taken for exercise performed independent of exercise machine 38.

Personal data 54 stored at computer system 10 may include information that is relevant to determining fitness gains in a workout such as weight, height, age, percentage body fat, bone density, metabolism, health problems, prescriptions, diet, and other health related factors. For example, food and liquid intake for a user may be monitored by a portable computer system as described in U.S. patent application Ser. No. 09/466,000 and in U.S. patent application Ser. No. 09/560,386, both herein incorporated by reference. In another example, medication intake for a user may be monitored by a portable computer system as described in U.S. patent application Ser. No. 09/560,992, herein incorporated by reference. Moreover, environmental exposure of a user may be monitored by a portable computer system as described in U.S. patent application Ser. No. 09/560,163, herein incorporated by reference.

In addition, personal data 54 preferably includes a user's output preference for how cumulative fitness activity should be output. For example, a user may prefer a particular font size, colors, output device, graphical application, etc.

Moreover, in personal data 54, an individual can designate multiple levels of security for accessing fitness profile 50, fitness goals 52 and personal data 54 stored on computer system 10. For example, particular parts of personal data 54 such as age and bone density may be shielded from transmittal and access without a password. As will be understood by one with ordinary skill in the art, multiple types of security methods and filters may be applied to fitness goals 52, personal data 54 and other data stored on computer system 10.

Fitness goals 52 preferably includes data such as target heart rates, target caloric loss, target distance and speed, and other target fitness goals stored in a data storage structure. In addition, fitness goals 52 preferably includes selections of control programs from control programs 56 for particular exercise machines and selected exercise sessions. In particular, a control program may be preselected in fitness goals 52 for a particular exercise machine such that the control program is automatically selected if a user selects to utilize that particular exercise machine. In addition, parameters for the control program, such as a level of difficulty, may also be included in fitness goals 52.

An exercise session may include multiple selections of control programs from among control programs 56 for multiple machines that the user is intended to utilize over a particular period of time. The session of selections of control programs may be pre-selected by the user, determined by a trainer, or selected by computer system 10 dependent upon the goals of the user and other factors. For example, a session may be selected that includes a control program for a 20-minute interval on a rowing machine at a particular speed and thereafter a control program for a 15-minute interval on a step machine with a target heart rate. In another example, a user enters fitness goals and a selection of available exercise machines and programs on those exercise machines is selected by computer system 10 and provided to the user.

As mentioned previously, if a user or trainer does not select exercise sessions for an individual, computer system 10 may provide suitable exercise sessions that are selectable by the individual or a trainer. In particular, computer system 10 is preferably enabled to determine sessions based on an individual's personal data 54, exercise machines available to the user, and fitness goals 52 provided such as the type of event training for, the date of the event and other pertinent data. Alternatively, fitness goals 52 may include weight loss, cardiovascular strengthening, muscle strengthening, etc. Preferably, an individual can enter or download specific types of exercise machines that are available in a personal gym or health club, wherein computer system 10 determines suitable exercise sessions based on machine availability.

A control program selection or session of control program selections in fitness goals 52 may be added to an electronic calendar 58 on computer system 10 in order to schedule for the user what type of exercise should be performed each day and how much time should be allotted for exercise. This function is particularly helpful for people wanting to follow a particular work out schedule. For example, athletes training for an event, such as a triathlon, where a schedule is imperative to reach fitness goals and where multiple diverse exercise modes are performed consecutively, would benefit from an exercise program stored on electronic calendar 58. In addition, a trainer may prescribe a particular workout schedule for a client on electronic calendar 58.

Control programs 56 preferably includes multiple control programs for controlling each of multiple types of diverse exercise machines. For example, for a treadmill, one control program may provide for a flat race while another control program may provide for a hill workout. Each of control programs 56 preferably designate a particular type of work out session with goals for reaching particular speeds, heights, heart rates, etc. dependent upon personal data 54. In particular, control programs 56 are preferably downloadable onto computer system 10.

The parameters of control programs 56 are advantageously adjustable by the user such that the intensity of each control program may be varied. For example, a user may select to utilize a particular control program, such as a hill workout, for thirty minutes one day and for forty-five minutes another day. Computer system 10 is preferably enabled to adjust the hill workout control program for varying times, difficulties, etc.

When computer system 10 connects to exercise machine 38, computer system 10 preferably detects the type of exercise machine from a machine type signal transmitted from exercise machine 38 in the common transmittable data structure format. In response to detecting the type of exercise machine, computer system 10 checks whether a control program for the detected exercise machine is designated in fitness goals 52. If a control program is not preselected, then a selection of control programs available for controlling the machine are displayed to the user via output interface 68. In response to a preselection of a control program or a current designation of a control program, with parameter selections, a machine control signal is transmitted from computer system 10 to exercise machine 38 in order to control the functions of exercise machine 38.

As a user exercises, the detected exercise signals received from exercise machine 38 are preferably compared with the goals of the exercise program. For example, a heart rate of the user may be compared with a target heart rate for the control program in view of personal data 54 or a current cumulative fitness activity level in fitness profile 50. If a user is not reaching target goals, an indicator may be output to the user via output interface 68 and/or the machine control signal to exercise machine adjusted to facilitate the user reaching target goals. If the user is exceeding target goals, an indicator may be output to the user via output interface 68 and/or the machine control signal adjusted to reduce exercise intensity.

As another feature of computer system 10, a user may compete against other users via a communications medium with other computer systems that are monitoring real-time fitness activity data, where the fitness activity data is transmittable in the common data structure format. For example, alternate computer system 59 is monitoring real-time fitness activity data on exercise machine 61. In particular, multiple users may be utilizing the same type of exercise machine or diverse types of exercise machines where a single type of display profile or multiple types of display profiles show each of the user's paces compared with the other user's. For example, one user may be riding a stationary bicycle while another user is running on a treadmill. A graphically rendered game may be displayed to each of the user's at each of the user's computer systems that are monitoring their exercise. The game or other application preferably compensates for the differences in types of exercise to show one user's position compared to another user's position in the game. The users may be within an area local to one another, such as in a gym, or may be within a global area and are connected via a network connection.

As previously described, output preferences may be included with personal data 54 on computer system 10. The user-designated output preference may designate output preferences for a particular type of output interface 68 for a particular user. Output interface 68 may include, but is not limited to including, a graphical display, an electronic paper, an audio speaker, audio headphones, a tactile detectable device, or a printer. The output preferences may include, but are not limited to specifications such as the size, type and coloring of a font in a graphical display, the type of tactile-detectable output (e.g. Braille), the language or the metric amount displayed.

In addition, the output preferences may designate a particular game or other program that adds a pictorial representation of a fitness profile. For example, a game that displays the user riding through a jungle forest may be selected. Moreover, alternative output device may be coupled to exercise machine 38 that provide additional media. For example, a user may switch stations, volume and signal bearing media on controllers including, but not limited to, a radio receiver, a television signal receiver, a compact disk player or a tape player that is accessible from exercise machine 38. In addition, as will be understood by one with ordinary skill in the art, any form of visual, auditory or tactile media may be provided for the individual to detect their fitness profile.

Computer system 10 is advantageously a portable computer system, such as a digital telephone, a personal digital assistant, a laptop computer, or a palmtop computer that is easily transportable and compact. In addition, computer system 10 is advantageously utilized as a personal exercise monitor for monitoring exercise across multiple diverse exercise machine platforms and a temporary controller for controlling movement of multiple diverse exercise machine platforms when in use by a user associated with computer system 10. It is important to note that a user is able to customize the features available on computer system 10. Since the user advantageously supplies computer system 10, the user may select the type and quality of desired output. For example, the user may download games, audio and other programs from signal-bearing media into data storage medium 51. In addition, the user may utilize a computer system that includes a color display, or alternatively a black and white display. In addition, it is important to note that computer system 10 may be continuously upgraded without requiring the upgrade of machine monitor 40.

In addition, it is important to note that the exercise machine monitoring system of the present invention may provide for a gym setting in which a user's account included in personal data 54 is charged as the user exercises and the user provides computer system 10 in order to control each of multiple diverse exercise machines. For example, a user's account may be debited per machine usage, per type of machine utilized, per time on the machine, per number of calories burned or other criteria. Moreover, a user's account may be debited for downloading a particular game or upgrade.

Figure 3:
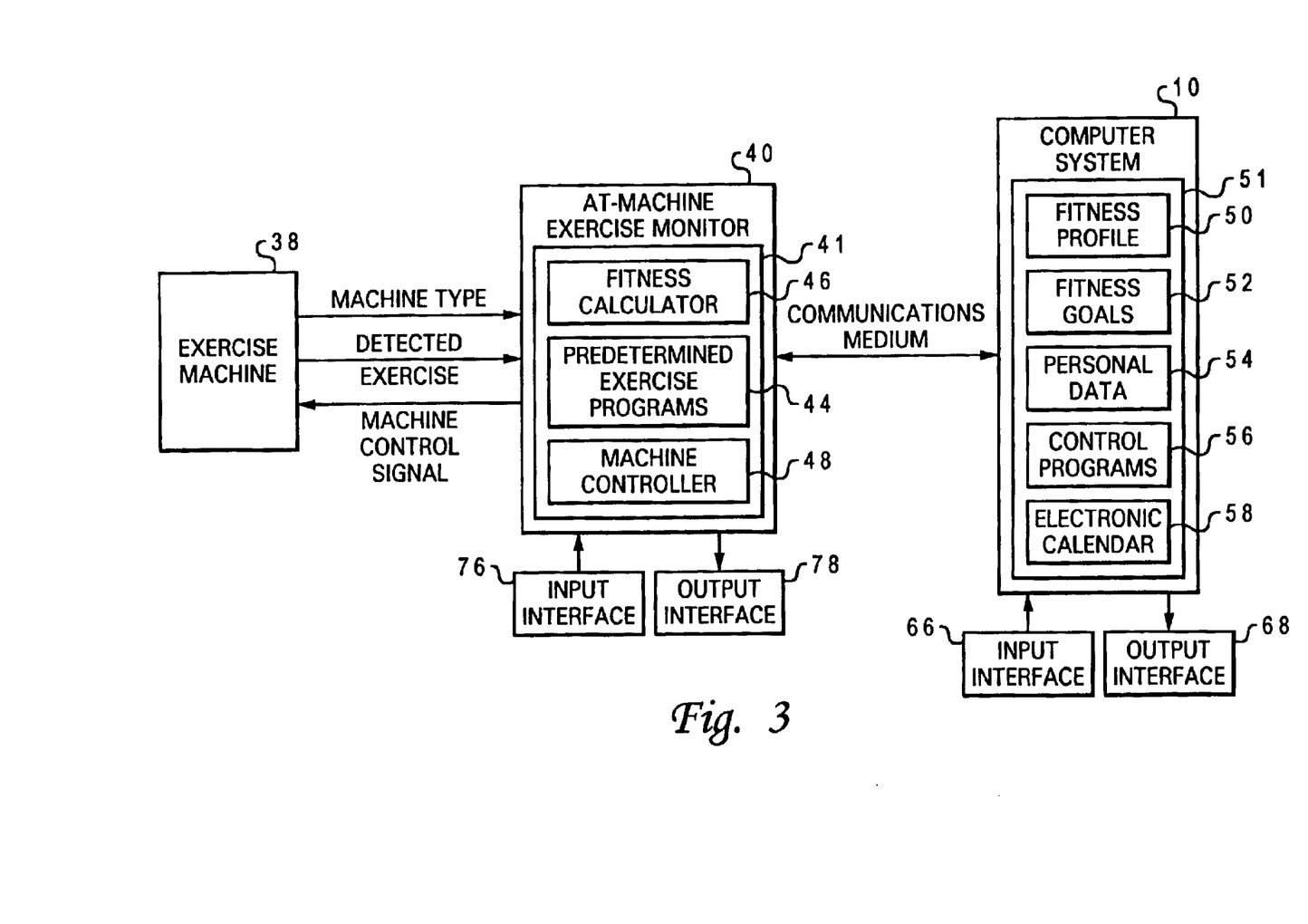
FIG. 3 depicts a second embodiment of a system for utilizing a personal electronic exercise monitor in accordance with the method, system and program of the present invention.

With reference now to FIG. 3, there is depicted a second embodiment of a system for utilizing a personal electronic exercise monitor in accordance with the method, system and program of the present invention. As depicted, an exercise machine includes an at-machine exercise monitor 40 that includes a fitness calculator 46, predetermined exercise programs 44, and a machine controller 48 within a data storage medium 41 accessible to said monitor 40.

At-machine exercise monitor 40 preferably enables a user to control exercise machine 38 both independently of computer system 10 and dependent upon computer system 10. Input interface 76 provides an interface for a user to enter personal data and select a predetermined exercise program from among predetermined exercise programs 44. Fitness calculator 46 calculates current fitness activity based on personal data and detected exercise signals. Machine controller 48 transmits a control signal to exercise machine 38 for controlling movement of exercise machine 38.

Alternatively, personal data may be transmitted from computer system 10 to at-machine exercise monitor 40. In addition, alternatively, a selection of a predetermined exercise program may be transmitted to at-machine exercise monitor 40. Moreover, alternatively, at-machine exercise monitor 40 acts as a "dumb terminal" receiving a control signal from computer system 10, such that exercise machine 38 is completely controlled by computer system 10.

Personal data transmitted from computer system 10 to at-machine exercise monitor 40 is preferably transmitted in an XML data file as shown below, where at-machine exercise monitor 40 is enabled to read the data file. In addition, a predetermined exercise program selection of program "5" for thirty minutes at exercise level "8" may be included in the data file. Moreover, an alternate form of XML formatting may be utilized.

<TimeStamp>888965153</TimeStamp>
<UserID>GeorgeG</UserID>
<Age>30</Age>
<Weight>180</Weight>
<Program>5</Program>
<ProgramTime>003000</ProgramTime>
<ProgramLevel>8</ProgramLevel>.

Figure 4:
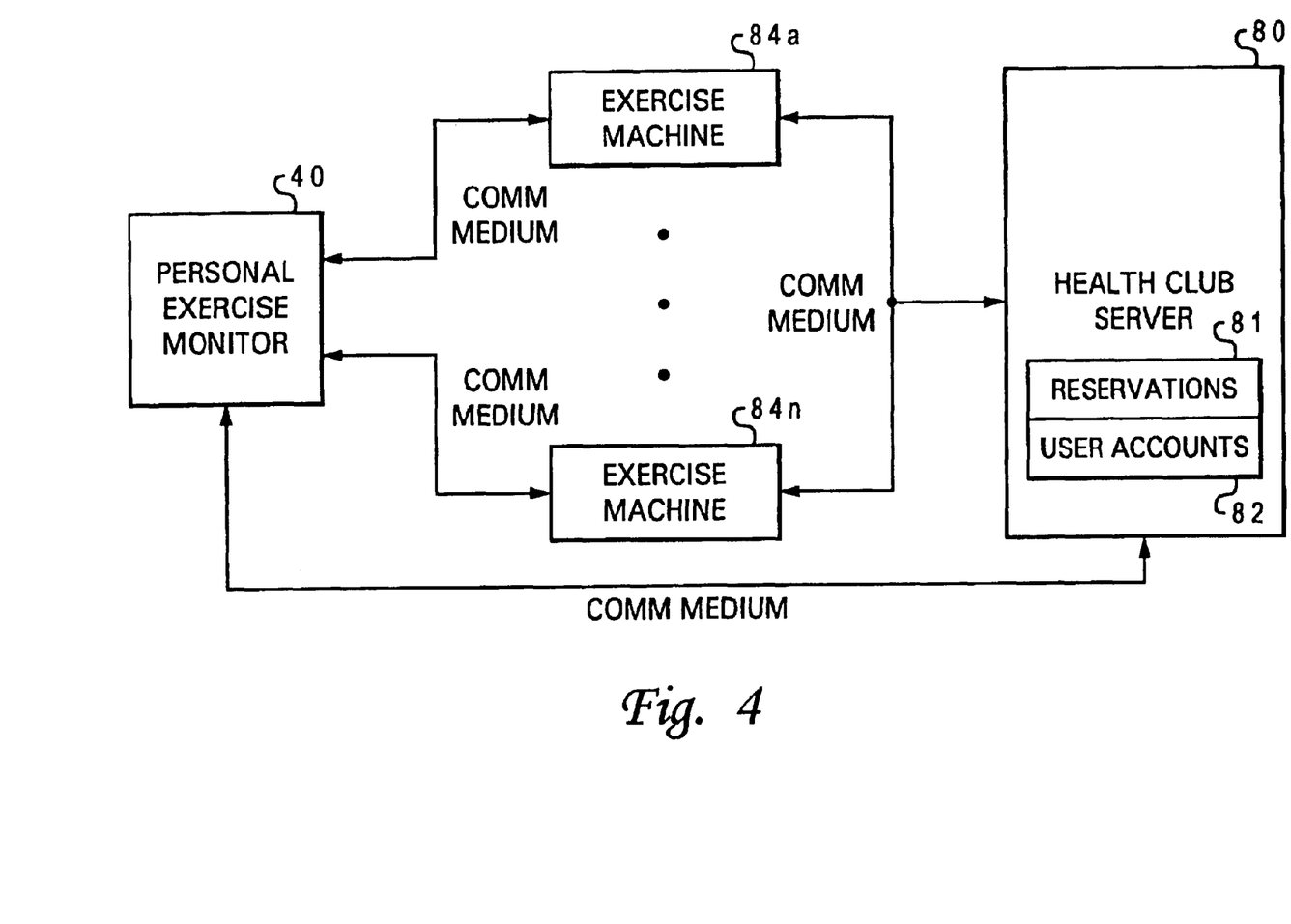
FIG. 4 illustrates one embodiment of a block diagram of a machine usage system for a health club in accordance with the method, system and program of the present invention.

Referring now to FIG. 4, there is illustrated a block diagram of a machine usage system for a health club in accordance with the method, system and program of the present invention. Computer system 10 is preferably enabled to transmit a schedule request for particular exercise machines during a particular time period in the common transmittable data structure format via a network connection such as the Internet or a LAN connected to a health club server 80. For example, an XML data file including a request for a "Tread505" exercise machine on Feb. 23, 2000 from 1 PM to 1:30 PM is depicted below. In addition, an alternate form of XML formatting may be utilized.

<TimeStamp>888965153</TimeStamp>
<UserID>GeorgeG</UserID>
<MachineRequest>Tread505</MachineRequest>
<MachineRequestDay>02.23.2000</MachineRequestDay>
<MachineReqTime>13:00:00,13:30:00</MachineReqTime>.

Health club server 80 preferably includes a reservation database 81 containing a listing of each exercise machine available and any reservations made for the machines. In addition, time limits for each exercise machine may be specified. In addition, health club server 80 preferably includes user accounts 82 that may include a prepaid debit amount, a credit card number, bank account number, or other financial information that can be utilized to charge a user for a particular service.

The reservation server 80 compares the schedule requests from computer system 10 with available time slots in reservation database 81 and transmits a list of available scheduling to computer system 10. The individual may then select to reserve exercise machines from the available scheduling. In scheduling time, an identifier and/or password for the user is transmitted and stored with the reservation. In addition, the individual may select to be placed on a waiting list for exercise machines that are currently reserved during a requested time period. Computer system 10 is then notified if the time slot opens. Preferably, a session of scheduled exercise machines is added to an electronic calendar or other scheduling database on computer system 10.

In addition, reservation server 80 may be connected to multiple at-machine exercise machines 84a–84n via a communications medium. Exercise machines 84a–84n communicate with computer system 10 to receive a reservation identifier for the user and transmit verification requests to reservation server 80 to verify that a user has a reservation for an exercise monitor being requested by that user. In verifying a user, both the reservation stored in reservation database 81 and the account information for the user stored in user accounts 82 are verified. In addition, the user account may be debited. In receiving a verification, exercise machines 84a–84n are enabled to function for the verified user.

Reservation server 80 preferably tracks statistical data concerning the times utilized and frequency of reservation requests for exercise machines. By tracking reservation data, marketing and financial planning data can be collected. For example, peak hours for a health club can be determined. In addition, by tracking reservation data, a member might be limited in the number of times that they can schedule a reservation and later cancel the reservation. Either periodically or in real-time, data from each of exercise machines 84a–84n may be transmitted to reservation server 80 in order to track the usage of each exercise machine. In an alternate embodiment, data collected at each of exercise machines 84a–84n may be transmitted periodically or in real-time via a wireless transmission medium to a server or other data storage medium that compiles data about the usage of each exercise machines 84a–84n. Thus, whether an exercise machine is in use in a home gym or a health club, a manufacturer or owner can obtain data about the usage of the exercise machine via communications with each exercise machines 84a–84n.

Figure 5:
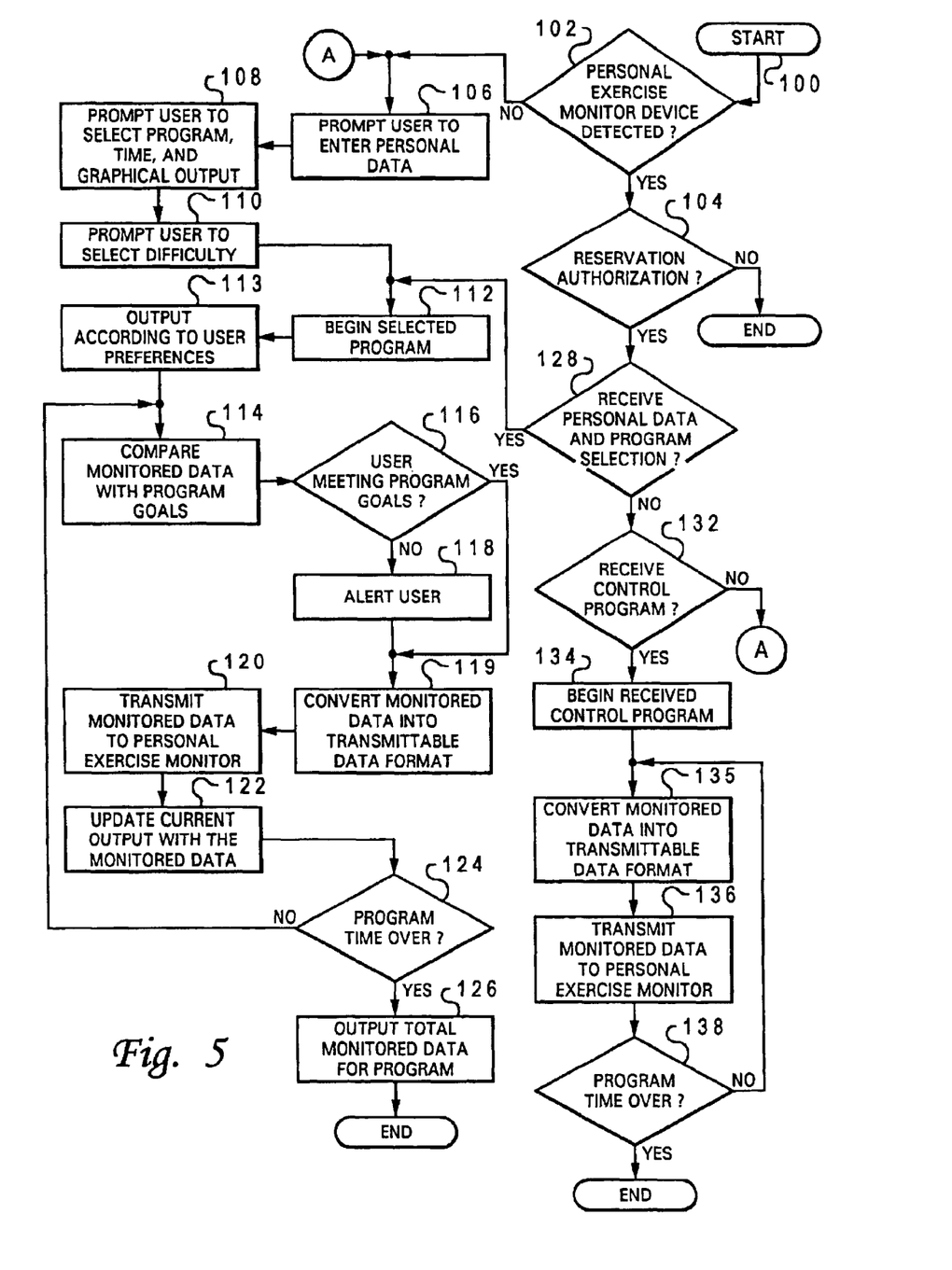
FIG. 5 illustrates a high level logic flowchart of a process and program for controlling an exercise machine in accordance with the present invention.

With reference now to FIG. 5, there is illustrated a high level logic flowchart of a process and program for controlling an exercise machine in accordance with the present invention. As depicted, the process starts at block 100 and thereafter proceeds to block 102. Block 102 illustrates a determination as to whether or not reservation authorization is received. In order for reservation authorization to be received the user must enter an identifier into a machine monitor or supply the identifier from a personal exercise monitor. If a reservation for the machine has been made, the identifier is compared with an identifier under which the machine is reserved. If there is a match, authorization is provided. Therefore, if authorization is not provided, the process ends. If authorization is provided, the process passes to block 104. Block 104 depicts a determination as to whether or not a personal exercise monitor is selected to control the exercise machine. If a personal exercise monitor is not selected, the process passes to block 106. If a personal exercise monitor is selected, the process passes to block 128.

Block 106 illustrates prompting the user to enter personal data such as age, weight, and height. Thereafter, block 108 depicts prompting the user to select a program, time duration and output preference for the program. Next, block 110 illustrates prompting the user to select a difficulty or speed of the program. Thereafter, block 112 depicts starting the selected program. Block 113 depicts controlling output of the monitored data and any other user-determined output according the user's output preferences to an output interface. Block 114 illustrates comparing monitored data with program goals. Next, block 116 depicts a determination as to whether or not the user is meeting the program goals. For example, meeting a program goal might include that a user's heart rate has reached a target level depending on the age and weight of the user. If the user is meeting the program goals, then the process passes to block 119. If the user is not meeting the program goals, then the process passes to block 118. Block 118 illustrates alerting the user that they are not within the program goals. The user is not within the program goals if the user does not reach the program goals or if the user exceeds the program goals. Next, block 119 depicts converting the monitored data into a common transmittable data format. Block 120 illustrates transmitting the monitored data to the personal exercise monitor. Thereafter, block 122 illustrates updating the current output with the monitored data. Next, block 124 depicts a determination as to whether or not the program for the machine is over. If the program is not over, the process passes to block 114. If the program is over, the process passes to block 126. Block 126 illustrates outputting totals of monitored data from the duration of the exercise program; and the process ends.

Returning to block 128, there is depicted a determination as to whether or not personal data and program selection are received. If personal data and program selection are received, then the process passes to block 112 and are utilized to set-up the at-machine exercise monitor. If personal data and program selection are not received, the process passes to block 132. Block 132 illustrates a determination as to whether or not a control program signal from a personal exercise monitor is received. If a control program signal is not received, the process defaults and passes to block 106. If a control program signal is received, the process passes to block 134. Block 134 depicts starting control of the exercise machine by the control program signal. Thereafter, block 135 illustrates converting the monitored exercise data into a common transmittable data format. Next, block 136 depicts transmitting monitored exercise data to the personal exercise monitor. Next, block 138 illustrates a determination as to whether the program time is over as designated by the control signal. If the program time is over, the process ends. If the program time is not over, the process passes to block 136.

Figure 6:
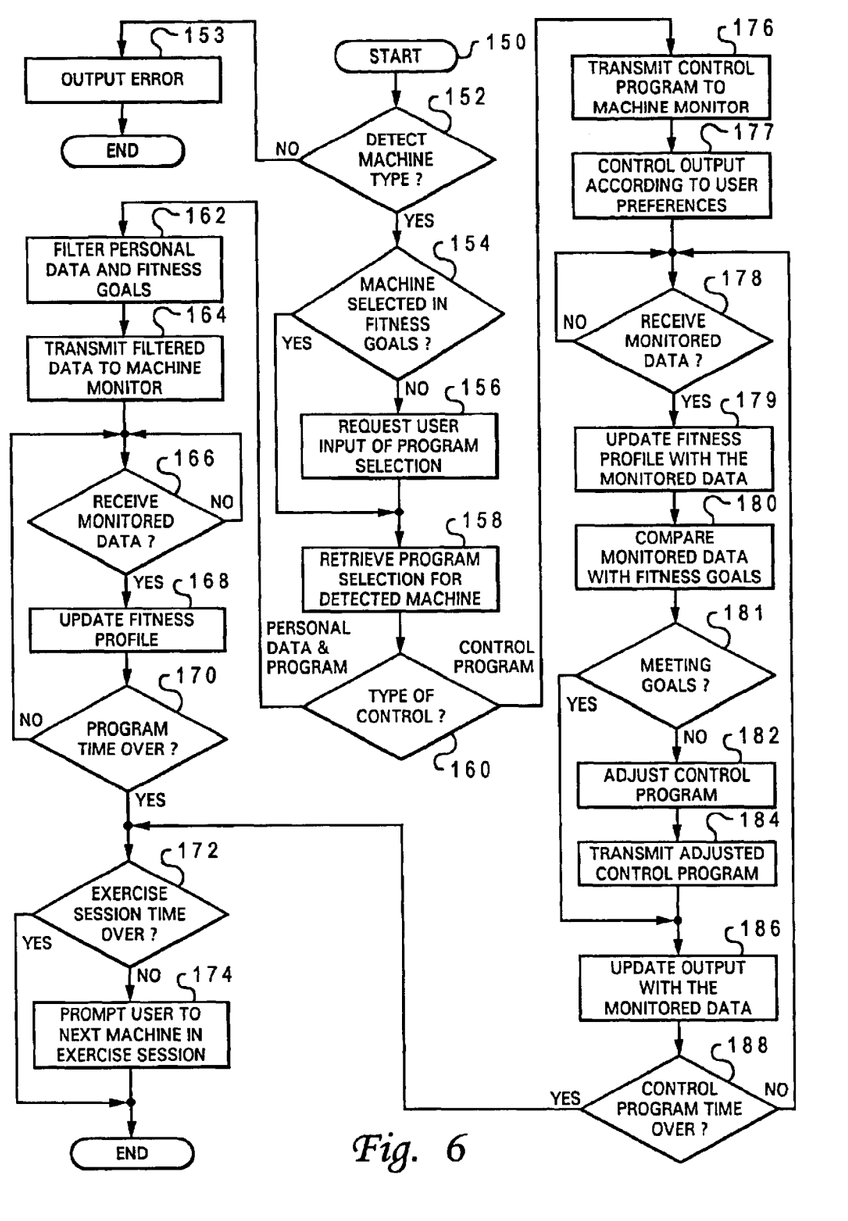
FIG. 6 depicts a high level logic flowchart of a process and program for utilizing a personal electronic exercise monitor to control an exercise machine in accordance with present invention.

Referring now to FIG. 6, there is depicted a high level logic flowchart of a process and program for utilizing a personal electronic exercise monitor to control an exercise machine in accordance with the present invention. As illustrated, the process starts at block 150 and thereafter proceeds to block 152. Block 152 depicts a determination as to whether or not a machine type is detected. A machine type may be detected from a signal from the exercise machine or from an entry via an input interface. If a machine type is not detected, the process passes to block 153. Block 153 illustrates an error; and the process ends. Alternatively, the process may perform a particular number of retries before ending. If a machine type is detected, the process passes to block 154. Block 154 depicts a determination as to whether or not the detected machine is included in the fitness goals. The detected machine may be selected as part of an exercise session, or a particular control program may be designated for the detected machine in the fitness goals. If the machine is not included in the fitness goals, the process passes to block 156. Block 156 illustrates requesting user input of a control program selection including difficulty; and the process passes to block 158. If the machine is included in the fitness goals, the process passes to block 158.

Block 158 depicts retrieving the selected program for the machine. Thereafter, block 160 illustrates a determination as to the control mode selection for the personal exercise monitor. If the control mode is set to transmit personal data and program selections the process passes to block 162. If the control mode is set to transmit a control program, the process passes to block 176.

Block 162 depicts filtering the personal data and program selection according to security filters. Next, block 164 illustrates transmitting the filtered data to the at-machine exercise monitor. Thereafter, block 166 depicts a determination as to whether or not monitored exercise data is received. If monitored exercise data is not received, the process iterates at block 166 for a period of time. If monitored exercise data is received, the process passes to block 168. Block 168 illustrates updating the fitness profile. Thereafter, block 170 depicts a determination as to whether or not the program time is over for the machine. If the program time is not over, the process passes to block 166. If the program time is over, the process passes to block 172. Block 172 illustrates a determination as to whether or not the exercise session is over. If the exercise session is over the process ends. If the exercise session is not over, the process passes to block 174. Block 174 depicts prompting the user to the next exercise machine for the session; and the process ends.

Block 176 depicts transmitting a control signal for the control program to the exercise machine. Next, block 177 illustrates controlling output of the cumulative fitness activity data according to user output preferences to an output interface. Thereafter, block 178 illustrates a determination as to whether or not monitored exercise data is received from the exercise machine. If monitored exercise data is not received, the process iterates at block 178. If monitored exercise data is received, the process passes to block 179. Block 179 illustrates updating the fitness profile with the monitored data. Next, block 180 depicts comparing the monitored data with the fitness goals and program. Next, block 181 illustrates a determination as to whether or not the user is meeting the fitness goals. If the user is not meeting the fitness goals, then the process passes to block 186. If the user is meeting the fitness goals, then the process passes to block 182.

Block 182 illustrates adjusting the control signal for the control program in order to aid the user in meeting the fitness goals. Next, block 184 depicts transmitting the adjusted control signal to the exercise machine. Block 186 illustrates updating the output interface with the monitored exercise data. Thereafter, block 188 depicts a determination as to whether or not the program time is over. If the program time is not over, the process passes to block 178. If the program time is over, the process passes to block 172.

Figure 7:
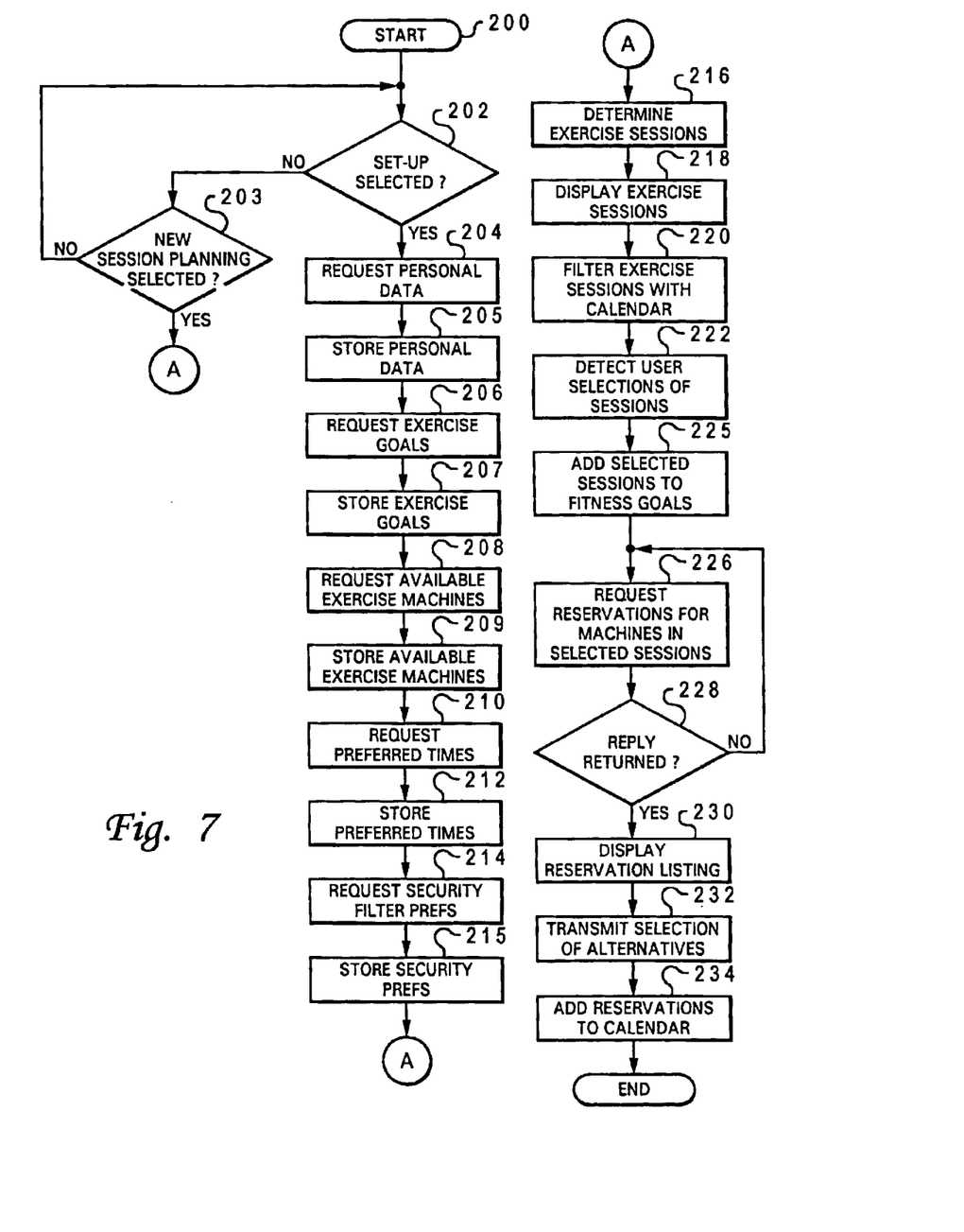
FIG. 7 illustrates a high level logic flowchart of a process and program for specializing a personal electronic exercise monitor in accordance with the present invention.

With reference now to FIG. 7, there is illustrated a high level logic flowchart of a process and program for specializing a personal electronic exercise monitor in accordance with the present invention. As depicted, the process starts at block 200 and thereafter proceeds to block 202. Block 202 illustrates a determination as to whether or not a set-up request is made. If a set-up request is made for a particular user, the process passes to block 204. Multiple users may utilize a single portable computer system as a personal exercise monitoring system. If a set-up request is not made, the process passes to block 203. Block 203 depicts a determination as to whether or not new session planning is selected. If new session planning is not requested, the process passes to block 202. If new session planning is requested, the process passes to block 216.

Block 204 depicts requesting personal data from the user. Thereafter, block 205 illustrates storing the personal data, preferably in a data storage structure. Next, block 206 depicts requesting fitness goals such as race goals, weight loss, cardiovascular strength, etc. Block 207 illustrates storing the fitness goals. Block 208 depicts requesting a list of exercise machines that are available to the user. The user may download the list of exercise machines, select from a list of preloaded exercise machines, or enter new exercise machines. Thereafter, block 209 illustrates storing the list of available exercise machines. Next, block 210 depicts requesting preferred exercise times. Block 212 illustrates storing the preferred exercise times. Next, block 214 depicts requesting security filter preferences. Block 215 illustrates storing the security filter preferences with the personal data. Thereafter, block 216 depicts determining an exercise session or sessions. Next, block 218 illustrates displaying the exercise session or sessions; and the process passes to block 220.

Block 220 illustrates filtering the displayed sessions with the user's calendar; and the process passes to block 222. Block 222 depicts detecting user selections of sessions. In addition to the personal exercise monitor determining suitable exercise sessions, the user may create his/her own sessions, or sessions may be downloaded from another source. In addition, a session may include control programs for a single exercise machines or for multiple diverse exercise machines. Next, block 225 depicts adding the selected sessions and output preferences to the fitness goals for the user. Thereafter, block 226 illustrates transmitting a request for reservations for the exercise machines included in the selected sessions. Next, block 228 depicts a determination as to whether or not a reply is received from a reservation server. If a reply is not received, the process passes to block 226. If a reply is received, the process passes to block 230. Block 230 illustrates displaying the reservation listing. Preferably the reservation listing includes exercise machines that have confirmed reservations and alternatives for unavailable machine requests. Block 232 depicts transmitting selections from alternatives. Block 234 illustrates adding the reservations to the user's electronic calendar; and the process ends.

Figure 8:
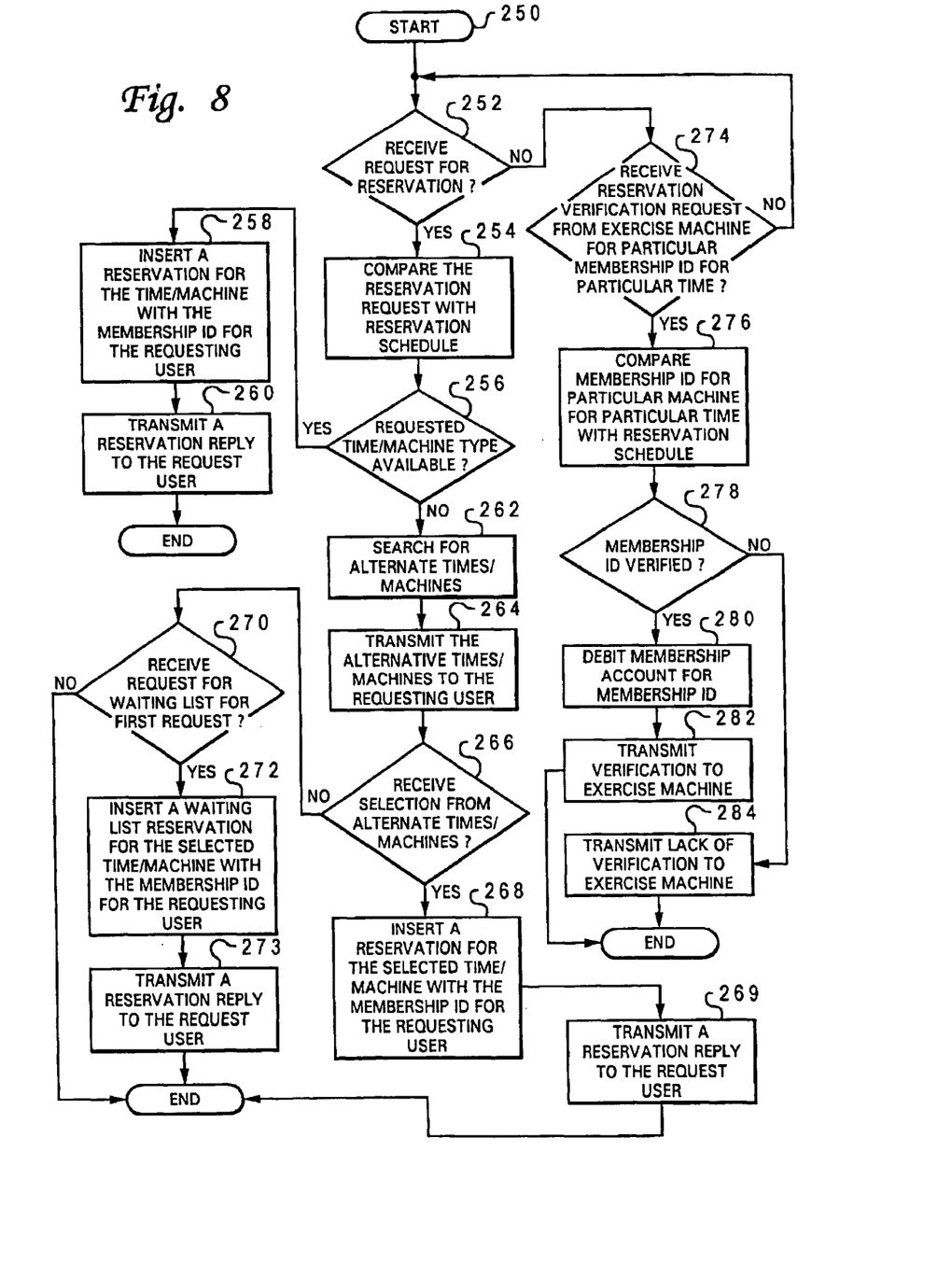
FIG. 8 depicts a high level logic flowchart of a process and program for controlling machine usage for a health club in accordance with the present invention.

Referring now to FIG. 8, there is depicted a high level logic flowchart of a process and program for controlling machine usage for a health club in accordance with the present invention. As depicted, the process starts at block 250, and thereafter proceeds to block 252. Block 252 depicts a determination as to whether or not a request for a reservation is received. If a request for a reservation is not received, then the process passes to block 274. If a request for a reservation is received, then the process passes to block 254. Block 254 illustrates comparing the reservation request with the reservation schedule at the health club server. Next, block 256 depicts a determination as to whether or not the requested machine type and time are available. If the requested machine type and time are not available, then the process passes to block 262. If the requested machine type and time are available, then the process passes to block 258. Block 258 illustrates inserting a reservation for the machine type and time in the reservation schedule with the membership id of the requesting user. Next, block 260 depicts transmitting a reservation reply to the portable computer system for the requesting user; and the process ends.

Block 262 depicts searching the reservation schedule for alternative times and exercise machine types. Next, block 264 illustrates transmitting the alternative times and exercise machine types to the portable computer system for the requesting user. Thereafter, block 266 depicts a determination as to whether or not a selection from among the alternatives is received at the health club server from the portable computer system for the requesting user. If a selection from among the alternatives is received, then the process passes to block 268. Block 268 illustrates inserting a reservation for the selected machine type and time in the reservation schedule with the membership id of the requesting user. Next, block 269 depicts transmitting a reservation reply to the portable computer system for the requesting user; and the process ends.

Returning to block 266, if a selection from among the alternatives is not received, then the process passes to block 270. Block 270 depicts a determination as to whether or not a request for the waiting list for the user's first machine type and time request is received. If a request for the waiting list is not received, then the process ends. If a request for the waiting list is received, then the process passes to block 272. Block 272 illustrates inserting a waiting list reservation for the machine type and time in the reservation schedule with the membership id of the requesting user. Next, block 273 depicts transmitting a reservation reply to the portable computer system for the requesting user; and the process ends.

Block 274 illustrates a determination as to whether or not a reservation verification request is received from a particular exercise machine for a particular membership id for a particular time. If a reservation verification request is not received, then the process passes to block 252. If a reservation verification request is received, then the process passes to block 276. Block 276 depicts comparing the membership id with the particular exercise machine and time in the reservation schedule. Next, block 278 illustrates a determination as to whether or not the membership id is verified in the reservation schedule. If the membership id is not verified, then the process passes to block 284. Block 284 depicts transmitting a lack of verification indicator to the requesting exercise machine; and the process ends. If the membership id is verified, then the process passes to block 280. Block 280 illustrates debiting the membership account for the membership id. The membership account may be debited according to the type of exercise machine, the length of reservation for the exercise machine or other criteria. Next, block 282 depicts transmitting a verification to the requesting exercise machine; and the process ends.

It is important to note that, although the present invention has been described in the context of a fully functional computer system, those skilled in the art will appreciate that the mechanisms of the present invention are capable of being distributed as a program product in a variety of forms, and that the present invention applies equally regardless of the particular type of signal-bearing media utilized to actually carry out the distribution. Examples of signal-bearing media include, but are not limited to, recordable-type media such as floppy disks or CD-ROMs and transmission-type media such as analogue or digital communications links.

While the invention has been particularly shown and described with reference to a preferred embodiment, it will be understood by those skilled in the art that various changes in form and detail may be made therein without departing from the spirit and scope of the invention.

What is claimed is:

1. A program for monitoring cumulative fitness activity for a user, residing on a computer usable medium having computer readable program code means, said program comprising:

means for receiving at least one type of exercise indicator signal associated with exercise performed by a particular user from a particular exercise machine in a common transmittable data format at a portable computer system provided by said particular user; and means for computing and storing current cumulative fitness activity for said particular user at said portable computer system utilizing said at least one type of exercise indicator signal and previously stored cumulative fitness activity data from prior exercise by said particular user at a plurality of diverse exercise machines, such that said portable computer system associated with said particular user monitors the real-time cumulative fitness activity of said particular user from said at least one type of exercise indicator signal currently received from said particular exercise machine.

2. The program for monitoring cumulative fitness activity according to claim 1, said program further comprising:

means for receiving said at least one type of exercise indicator signal in an extensible mark-up language data format.

3. The program for monitoring cumulative fitness activity according to claim 1, said program further comprising:

means for receiving exercise indicator signals indicating exercise performed by a particular user from monitoring systems that monitor exercise indicator signals for said particular user independent of said particular exercise machine.

4. The program for monitoring cumulative fitness activity according to claim 1, said program further comprising:

means for receiving exercise indicator signals indicating exercise performed by a particular user from user input to an input interface coupled to said portable computer system.

5. The program for monitoring cumulative fitness activity according to claim 1, said program further comprising:

means for computing said current cumulative fitness activity according to said at least one type of exercise indicator signal, said previously stored cumulative fitness activity data, and personal data for said particular user.

6. The program for monitoring cumulative fitness activity according to claim 1, said program further comprising:

means for computing said current cumulative fitness activity according to said at least one type of exercise indicator signal, said previously stored cumulative fitness activity data, and additional health factors detected for said particular user at said portable computer system.

7. The program for monitoring cumulative fitness activity according to claim 1, said program further comprising:

means for computing said current cumulative fitness activity according to said at least one type of exercise indicator signal, said previously stored cumulative fitness activity data, and environmental exposure detected for said particular user at said portable computer system.

8. The program for monitoring cumulative fitness activity according to claim 1, said program further comprising:

means for distinguishing storage of said portion of said current cumulative fitness activity computed from use of said particular exercise machine.

9. The program for monitoring cumulative fitness activity according to claim 1, said program further comprising:

means for retrieving said previously stored cumulative fitness activity data by distinct sessions of exercise performed by said particular user across said plurality of diverse exercise machines.

10. The program for monitoring cumulative fitness activity according to claim 1, said program further comprising:

means for prompting said particular user, at said portable computer system, to utilize said particular exercise machine according to a predetermined exercise schedule for said particular user.

* * * * *